US00PP26079P3

(12) United States Plant Patent
Egger

(10) Patent No.: US PP26,079 P3
(45) Date of Patent: Nov. 10, 2015

(54) ***SEDUM* PLANT NAMED 'TOUCHDOWN FLAME'**

(50) Latin Name: ***Sedum telephium* (Syn. *Hylotelephium telephium*)**
Varietal Denomination: Touchdown Flame

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 220 days.

(21) Appl. No.: 13/998,104

(22) Filed: Sep. 30, 2013

(65) Prior Publication Data

US 2015/0096093 P1 Apr. 2, 2015

(51) Int. Cl.
*A01H 5/02* (2006.01)

(52) U.S. Cl.
USPC ..... Plt./479
CPC ..... *A01H 5/02* (2013.01)

(58) Field of Classification Search
USPC ..... Plt./479
See application file for complete search history.

(56) References Cited

PUBLICATIONS

Germania Seed Company. Emerald Coast—Ornamental Grasses and Perennials, retrieved on Jun. 18, 2015, retrieved from the Internet at <https://www.germaniaseed.com/pdf/2014/722_emeraldcoast.pdf> (2013-2014) pp. 1-13.*

Greenhouse Grower. Terra Nova Nurseries Announces New Sedum Touchdown Collection Aug. 15, 2013 retrieved on Jun. 17, 2015, retrieved from the Internet at <http://www.greenhousegrower.com/varieties/terra-nova-nurseries-announces-new-sedum-touchdown-collection/> 5 pp.*

* cited by examiner

*Primary Examiner* — June Hwu
(74) *Attorney, Agent, or Firm* — Klarquist Sparkman, LLP

(57) ABSTRACT

A new and distinct hybrid of *Sedum* plant substantially as shown and described, with creamy yellow flowers, dark red brown to green leaves, strong, dark red stems, multiple crowns, a dense, low, arching habit, and excellent vigor.

2 Drawing Sheets

Botanical denomination: *Sedum telephium* (Syn. *Hylotelephium telephium*).

Variety designation: 'Touchdown Flame'.

BACKGROUND OF THE INVENTION

The present invention relates to a new and distinct cultivar of *Sedum telephium* and given the cultivar name of 'Touchdown Flame'. *Sedum* is in the family Crassulaceae. The new cultivar is part of a planned breeding program to make short, compact, multicrown plants. The new cultivar originated from a cross of between *Sedum* 158-2, a proprietary, unselected seedling as the seed parent and *Sedum* 235-2, a proprietary, unselected seedling as the pollen parent.

Compared to the seed parent, *Sedum* 158-2, the new cultivar, has a much better habit and creamy yellow flowers rather than light pink.

Compared to the pollen parent, *Sedum* 235-2, the new cultivar has larger, greener leaves and a lower habit.

Compared to *Sedum* 'Desert Blonde', U.S. Plant Pat. No. 24,901, the new cultivar has foliage that is dark red brown to green rather than gray green and flowers that are more yellow.

This new and unique *Sedum* is distinguished by:

1. creamy yellow flowers,
2. dark red brown to green leaves,
3. strong, dark red stems,
4. multiple crowns,
5. a dense, low, arching habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 16 month old plant of the new cultivar in mid-May in the trial bed in Canby, Oreg.

FIG. 2 shows a 17 month old *Sedum* 'Touchdown Flame' growing in the garden in early June in Canby, Oreg.

FIG. 3 shows a 2 year old plant of *Sedum* 'Touchdown Flame' with flowers and fruit in the garden in July in Canby, Oreg.

DETAILED PLANT DESCRIPTION

The following is a detailed description of the new *Sedum* hybrid based on observations of 10 month old specimens grown in the trial bed in full sun under typical outdoor conditions in Canby, Oreg. Canby is Zone 8 on the USDA Hardiness map. Temperatures range from a high of 95° F. in August to 32°F. in January. Normal rainfall in Canby is 42.8 inches per year. The color descriptions are all based on *The Royal Horticultural Society Colour Chart,* 5th edition.

Plant:

*Type*.—Herbaceous perennial.

*Hardiness*.—USDA Zone 4 to 9.

*Size*.—23 cm tall from the ground to the top the inflorescence and 38 cm wide.

*Habit*.—Low, clumping mound.

*Vigor*.—Excellent.

Stem:

*Number*.—About 7.

*Size*.—11 cm long and 5 mm wide.

*Internode length*.—1 cm to 5 cm long.

*Color*.—Red Purple 59A.

*Texture*.—Succulent.

*Surface*.—Glabrous.

Leaf:

*Type*.—Simple.

*Arrangement*.—Opposite.

*Shape*.—Ovate.

*Apex*.—Acute.

*Base*.—Obtuse.

*Venation*.—Pinnate.

*Margins*.—Coarsely serrate.

*Blade size*.—Grows to 12.5 cm long and 7 cm wide, average size 4 cm to 8.5 cm long and 2.2 cm to 4 cm wide.

*Surface*.—Glabrous on both sides.

*Texture*.—Thick, spongy, succulent.

*Petiole*.—Leaves sessile.

*Leaf color*.—Topside early spring Yellow Green 147C on young leaves both sides transitioning to Red Purple 187A as leaves mature (transitioning leaves with veins Red Purple 187A near base) with bottom side Yellow Green 147C including vein; spring Red Purple 187A when mature, bottom side Yellow Green 147C tinted Greyed Purple 187A; topside summer to fall between Greyed Purple 187A and Brown 200A with the vein Greyed Purple 187A; bottom side Yellow Green 147C tinted Greyed Purple 187A with the vein Yellow Green 146C.

Inflorescence:

*Type*.—Terminal, corymbose, umbel-like.

*Number of flowers*.—500 to 1000 per stem (increases with age).

*Pedicels*.—1 mm long, 1 mm wide, glabrous, Yellow Green 147B.

*Peduncle*.—Grows to 7 cm tall and 4 mm wide, Greyed Purple 187B, glabrous.

*Size*.—Grows to 18 cm deep and 12 cm wide.

*Bloom period*.—August through October in Canby, Oreg.

Flower bud:

*Size*.—2.5 mm wide, 3 mm deep.

*Description*.—Ovoid.

*Color*.—White 155B tinted Red Purple 59C at the tip.

Flower:

*Type*.—Actinomorphic.

*Shape*.—Stellate.

*Size*.—3 mm deep and 3 mm wide.

*Corolla description*.—3 mm deep and 3 mm wide, 5 petals, each lanceolate, 4 mm long and 2 mm wide, margins entire, tip acuminate, glabrous on both sides, top side Yellow 4D, bottom side White 155B tinted Red Purple 59C at the tip.

*Calyx description*.—2 mm deep and 2 mm wide, stellate, 5 lobes, divided to the base, margins entire, tip acute, glabrous, Yellow Green 147C with margins Red Purple 187A on both sides.

*Stamen description*.—10, 3.1 mm long, filaments 3 mm long and White NN155C, anthers Red Purple 59A, no pollen.

*Pistil description*.—5 separate prominent carpels, each 2 mm deep and 1.5 mm wide, Yellow 4C overall, style 2 mm long.

*Fragrance*.—None.

*Lastingness*.—Each stem lasts up to a month.

Fruit:

*Type*.—Ventrally dehiscent follicle, erect, attenuate.

*Fertility*.—Low.

*Size*.—4 mm wide and 5 mm deep.

*Color*.—Yellow Green 145C surrounded by Greyed Orange 177A.

Seed: None seen.

Disease and pest resistance or tolerance: Pest and disease resistance are typical for this type of *Sedum*. No known resistances.

I claim:

1. A new and distinct hybrid of *Sedum* plant as herein illustrated and described.

* * * * *

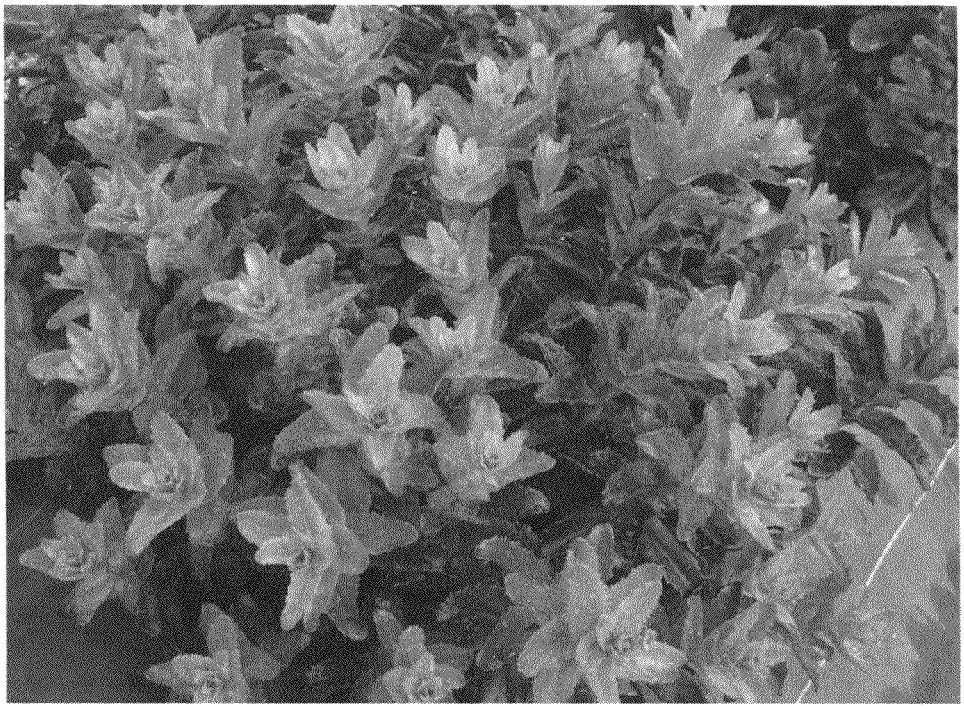
FIG. 1 above, FIG. 2 below
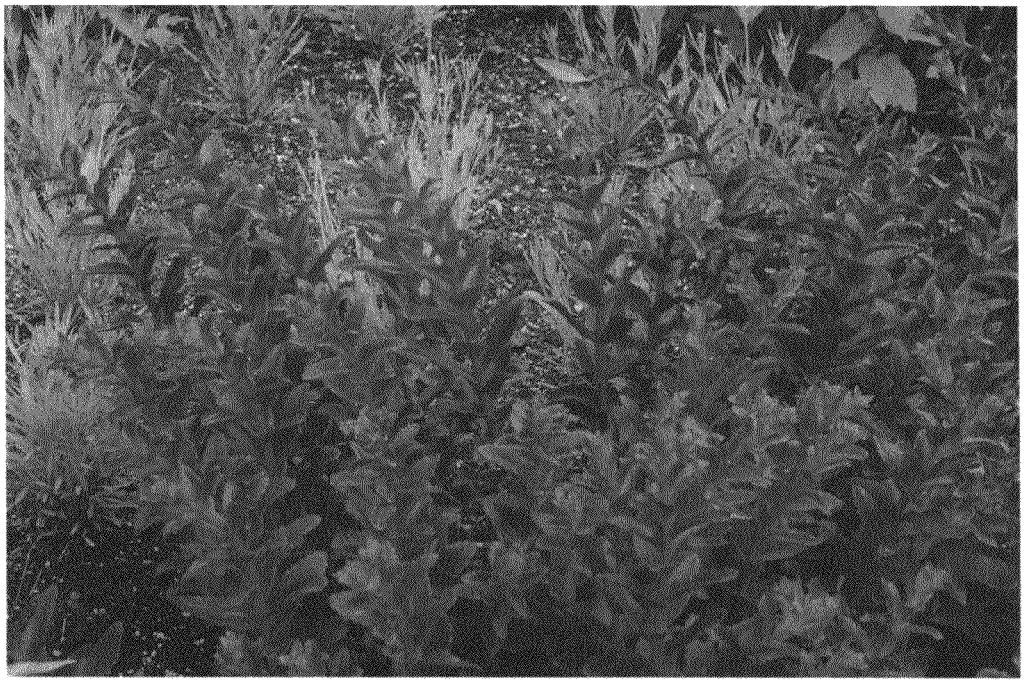

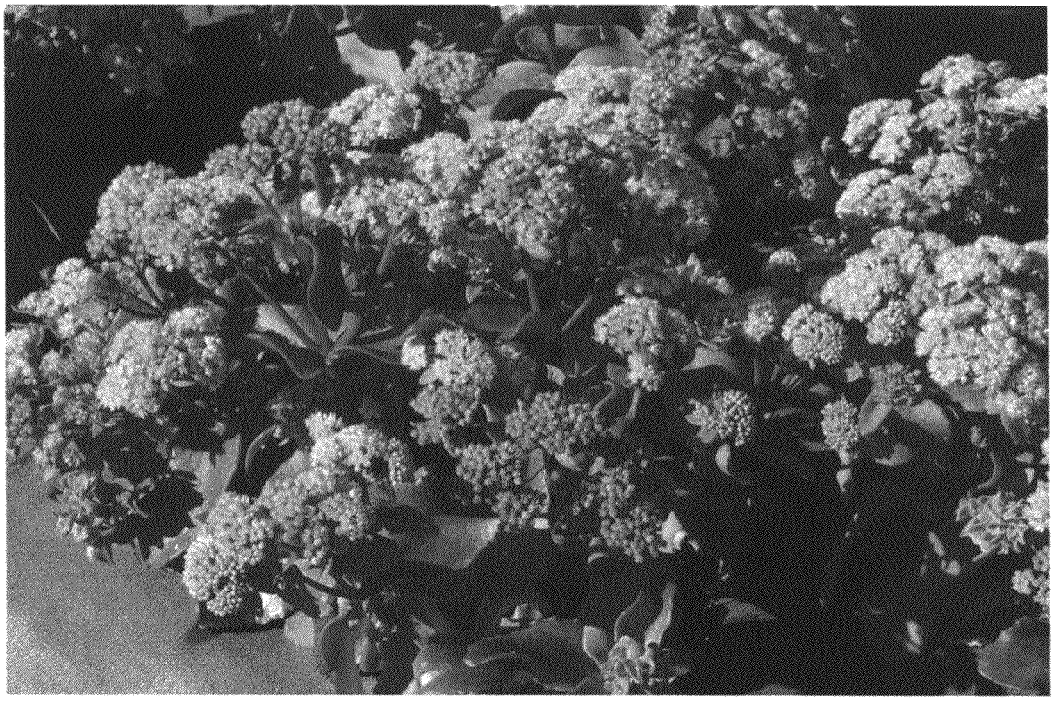
FIG. 3 above